United States Patent [19]

Smith, Jr.

[11] 4,203,672
[45] May 20, 1980

[54] SCANNING BEAM DISPLACEMENT COMPENSATION CONTROL SYSTEM

[75] Inventor: Edmund H. Smith, Jr., Wilmington, Del.

[73] Assignee: E. I. Du Pont de Nemours and Company, Wilmington, Del.

[21] Appl. No.: 743,003

[22] Filed: Nov. 18, 1976

[51] Int. Cl.$^2$ ............... G01N 21/18; G01B 11/26
[52] U.S. Cl. ............... 356/431; 356/400; 250/563; 250/235
[58] Field of Search .............. 356/199, 200, 172; 250/563, 571, 572, 211 K, 230, 203 R, 235; 350/6, 7

[56] References Cited

U.S. PATENT DOCUMENTS

| | | | |
|---|---|---|---|
| 3,198,951 | 8/1965 | Lentze | 250/563 |
| 3,364,813 | 1/1968 | McKinney | 250/230 X |
| 3,646,568 | 2/1972 | Woywood | 346/108 |
| 3,667,846 | 6/1972 | Nater et al. | 250/572 X |
| 3,715,599 | 2/1973 | Marcy | 356/106 |
| 3,809,806 | 5/1974 | Walker | 178/7.6 |
| 3,843,890 | 10/1974 | Anthony et al. | 250/563 |
| 3,966,329 | 6/1976 | Dickey | 356/172 |
| 3,975,640 | 8/1976 | Boux et al. | 250/385 |

OTHER PUBLICATIONS

J. Helmberger et al., Correction of Axial Deflection Errors in Rotating Mirror Systems, 12/75, pp. 249–251.

Primary Examiner—Vincent P. McGraw
Assistant Examiner—Rodney B. Bovernick

[57] ABSTRACT

An electro-optical system for the repetitive repositioning of a cyclically moving beam of radiation to a preselected point in space, particularly as applied to electro-optical web inspection.

14 Claims, 8 Drawing Figures

SCANNING BEAM DISPLACEMENT COMPENSATION CONTROL SYSTEM

BRIEF SUMMARY OF THE INVENTION

Generally, this invention relates to a closed loop circuit for the repetitive repositioning of a cyclically moving beam of radiation to a preselected point in space comprising a photosensitive detector disposed at the preselected point in space with photosensitive surface oriented toward the radiation beam, the radiation beam impinging on the photosensitive surface and developing a position-dependent electrical signal inclusive of a distinctive portion thereof representative of coincidence of the radiation beam with the preselected point in space, and radiation beam deflection means responsive to the electrical signal bringing the radiation beam into close conformity with the preselected point in space.

BACKGROUND

Tracking control of radiation flying spot scanning systems is desirable in the wire transmission of picture material, in television scanning apparatus and, particularly, in the close tolerance inspection of rapidly moving product webs. This invention is hereinafter described relative to flying spot web inspection, where it has become more and more difficult to inspect relatively wide webs, due to increasing manufacturing speeds, with scanning beams having small cross sections, e.g., on the order of 1 mm dia., to detect small pin hole type defects without danger of gaps occurring in the scan coverage of the inspected product and, of course, without spurious signal generation.

Of particular concern is the attention given to the mechanical and optical design of scanning systems, especially with respect to the effects of vibration, component misalignment, component manufacturing precision, scanner motor-bearing play, temperature changes and the like, which all have an effect on the tracking of a scanning radiation beam.

For example, multifaceted rotating mirror cone angle variations, i.e., the angle which each facet makes with the scanner axis of rotation, usually varying between ±0.05 m rad and ±0.15 m rad, cause corresponding scan path displacements. In addition, temperature changes can introduce still other variations in rotating mirror cone angles, or further distort the inspection system support framework to affect optical alignment.

The prior art teaches solutions of some of the adverse problems bearing on the constancy of scan-to-scan spacing, especially as regards information recording using light beams. However, no one has devised a way to compensate for these influences effectively at extremely high scanning rates. The usual technique has included the use of beam splitters to form an auxiliary monitoring beam from the main scanning beam, as taught in IBM Technical Disclosure Bulletin, Vol. 15, No. 1, June, 1972, "Deflection Sensor for Optical Scanners" by D. H. Casler, D. R. Cecchi and W. D. McNeil; U.S. Pat. No. 3,715,599 issued Feb. 6, 1973 to R. Marcy, entitled "Electro-Optical System for Controlling the Attitude of a Stage Mounted on a Carriage Sliding Along a Parallel Bench"; and U.S. Pat. No. 3,646,568 issued Feb. 29, 1972, entitled "Beam Control System". To avoid the additional optical losses introduced by the use of beam splitters in a flying spot inspection system, an alternate accepted practice has been to apply a programmed set of predetermined control voltages to the beam deflector to correct for each rotating mirror facet's known variation from a norm, as taught in U.S. Pat. No. 3,809,806 issued May 7, 1974 to Walker et al., entitled "Banding Correction System for Film Recording Apparatus", and the article entitled "Correction of Axial Deflection Errors in Rotating Mirror Systems" by J. Helmberger et al., Optics and Laser Technology, Dec. 1975, pp. 249–252.

DRAWINGS

The following drawings constitute part of this specification, in which.

THE INVENTION

As regards web inspection, this invention relates to an apparatus and method for compensating undesirable machine direction and torsional optical path displacements in flying spot scans across a product web caused by the effects of vibration, temperature change, rotating mirror facet-to-facet variation or optical system misalignment.

In one embodiment, two specially configured photocell assemblies disposed adjacent the edges of the moving product web are used to produce the displacement and torsion error signals required to cause beam deflector means to restore straying scans to a preselected linear cross-product path. In this way, no gaps in scan coverage of the moving product are permitted to form.

Although other photosensitive detectors can be used to generate the scan path displacement signals, such as a dual cell photomultiplier, a photoconductor or a photovoltaic cell, photocell detectors have been chosen for purposes of the following detailed description.

For systems using the scan autocalibration technique taught by Anthony et al. in U.S. Pat. No. 3,843,890 issued Oct. 22, 1974, of common assignment herewith, the AUTOCAL siganl amplitude is ratioed with the amplitudes of signals generated as the scan beam passes through two amplitude-graded optical filters disposed at the beginning and end of the scan path, respectively, and thus generate the requisite machine direction (MD) displacement and the scan torsion correction signals.

Extensive investigation of beam path distortions encountered in high speed web inspection scanning systems has shown that these have been caused by a composite of certain cyclical mechanical and thermal factors such as: frame-transmitted vibrations, scanner bearing play, mirror facet cone angle variations, thermal variations causing scanner or collector optical misalignment and the like. The beam path distortions with components in the plane of the product web, particularly those running in the machine direction (MD), are usually of sufficient amplitude to warrant their compensation. With the exception of the mirror facet cone angle variations, which occur in a step-wise fashion at the scanning rate, typically 2400 Hz, the remaining factors are, in general, smooth time-varying functions limited to frequencies below about 200 Hz. Thus, within each cycle of a typical variation, usually ten or more scans will occur. The result is that the incremental change in MD direction beam path distortion between scan beginning and ending points is, in most cases, negligible, and the initial MD displacement compensation (mainly for mirror facet cone angle variation) at the outset of each scan is sufficient to maintain the scan line along its predetermined path in space. This compensation is effected by photocells 5A and 5B, which the scanning beam 1a traverses before ever reaching the lefthand edge of the web, as seen in FIG. 1.

Figure 1:
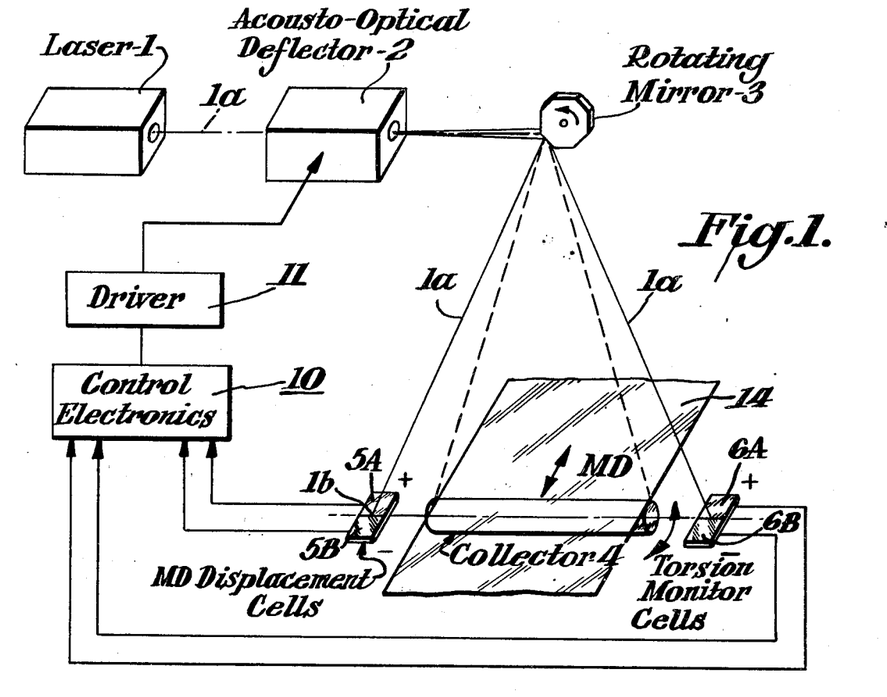
FIG. 1 is a partially schematic perspective view of a preferred embodiment of an inspector scan system showing the relationship of the beam displacement compensation control system elements with one another.

A second compensation scheme is used to neutralize beam path distortions having significant torsional components, i.e., those which tend to displace the scan line around a vertical axis drawn to the left-hand end of light collector 4 of FIG. 1. Since these variations also have frequency components significantly below the scanning rate, essentially complete compensation can be effected by applying compensatory beam deflection over the full duration of a single scan based upon the beam path displacements sensed at the beginning and end of the preceding scan. Accordingly, photocells 6A and 6B, disposed just off the right-hand edge of web 14, are reserved to compensate for the torsional components.

Generally, the two compensations mentioned are all that are required for good beam tracking control and the following description is therefore concerned solely with these two types of beam path distortions.

Referring to FIG. 1, a preferred embodiment of my invention, as applied to the scanning inspection of a running web 14, comprises a continuous wave (CW) laser source 1, typically a Spectra Physics Model 120 HeNe type, which produces a collimated monochromatic beam 1a, with optics not shown, which is directed through an acousto-optical beam deflector 2, typically a Model 1205-1 Deflector driven by a driver 11, typically a Model D 101-1, the deflector and driver both being marketed by Isomet Corporation.

By generating a series of regularly spaced acoustic wavefronts in the acoustic material, appropriately driven acousto-optical beam deflector 2 causes an incident monochromatic laser beam to separate into m ordered diffracted components at discrete exit angles, $\phi$, according to the Bragg equation:

$$m\lambda = 2d \sin(\phi/2)$$

where m is the diffracted order of the exit beam,
  $\lambda$ is the wavelength of the incident laser beam,
  d is the lattice spacing ($\Lambda$) of the acoustic medium as a function of the exciting carrier frequency, and
  $\phi$ is the beam exit angle referred to the direction of the undeviated zero-order beam.

An optical stop (not shown) is used to block the zero order as well as the second and higher order diffracted beams, after which the first order beam is directed upon the rotating facets of mirror 3. Incidentally, a collimated beam 1a is not absolutely essential; however, the spot cross-section 1b should, of course, always be contained within the photosensitive area of the detectors 5A, 5B and 6A, 6B, which collimation does ensure.

The first order diffracted beam produced in beam deflector 2 is directed to strike the moving facets of rotating mirror 3. Rotating mirror 3 is provided with, typically, 12 to 16 carefully aligned (i.e., the cone angles are typically within ±0.15 m. rad) mirror facets, which each direct the beam spot 1b in linear paths on repeated scans transversely across two identical photocell assemblies 5A, 5B and 6A, 6B and running product web 14. Radiation transmitted by web 14 is collected in radiation-conducting rod collector 4 and is analyzed for three different classes of defects, all as described in Anthony et al. U.S. Pat. No. 3,843,890, of common assignment.

This invention is directed exclusively to scanning beam tracking control during traversals of the web, and not to web inspection per se.

Figure 2:
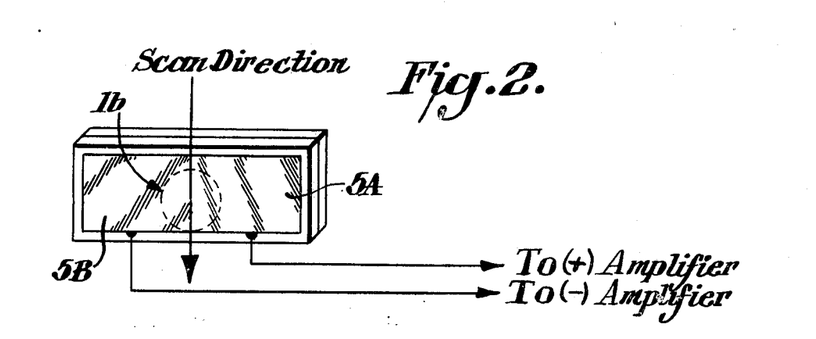
FIG. 2 is a partially schematic perspective view of a sectored photocell construction which can be utilized with the apparatus of FIG. 1.

The dual photocell assemblies used in the FIG. 1 apparatus are detailed in FIG. 2 for the 5A, 5B photosensitive detector (6A, 6B being of identical construction) and each comprises two silicon type photocells, each having a scan direction dimension of 2 cm and a combined width dimension of 2 cm, disposed in opposed electrical orientation one to the other at a separation of about 0.1 mm width (not shown), thereby separating the cells electrically. The inspection beam spot 1b is drawn in for the electrically balanced state when the beam spot overlies cells 5A and 5B to the same area extent, the beam traversing web 14 of FIG. 1 in the arrow-denoted Scan Direction. For the polarities indicated, cell 5A generates a positive d-c voltage signal AA (FIG. 3A) at the output of amplifier 12A whereas cell 5B generates a negative d-c voltage signal BB (FIG. 3A) at the corresponding output terminal of amplifier 12B (FIG. 3), both of which amplifiers are housed in the control electronics block 10, FIG. 1. Typically, when spot 1b overlies cell 5A to a greater extent than cell 5B, the resultant MD error signal generated by this photocell pair, waveform EE, is used to produce MD displacement correction signal, waveform FF.

A second photocell assembly 6A, 6B, in all respects identical with 5A, 5B, disposed just off the right-hand edge of the web generates the torsion error signal (waveform LL) corresponding to the torsional beam displacement from the preselected cross web path, which in turn is used to produce torsion correction signal, waveform RR.

During each interscan interval, electronic control circuit 10 computes the linear correction voltage profile needed to be applied to driver 11 which can, typically, be a voltage-controlled oscillator (VCO). Driver 11 responds to the control signal by applying a frequency-modulated RF carrier signal, whose frequency varies about a predetermined center frequency, to the input terminals of acousto-optic beam deflector 2. The center frequency is selected so as to optimize the intensity of the first order diffracted beam from the deflector (i.e., the Bragg condition).

It should be mentioned that other types of beam deflectors 2 can be used, such as electro-optic and mirror or glass plate galvanometer scan types. With a monochromatic laser source, the acousto-optic beam delfector is preferred, because it is particularly responsive to the high scan rates required for web inspection applications.

Although mirror 3 facet cone angle variation, inherent in the rotating mirror design, normally results in significant scan-to-scan shifts in MD position of the scan beam at its starting point along the leading edge of the beginning scan photocell sensor 5A, 5B, the apparatus is designed to restore the beam to its prescribed MD starting position before the beam completes its transit of the 5A, 5B sensor surface.

Figure 3:
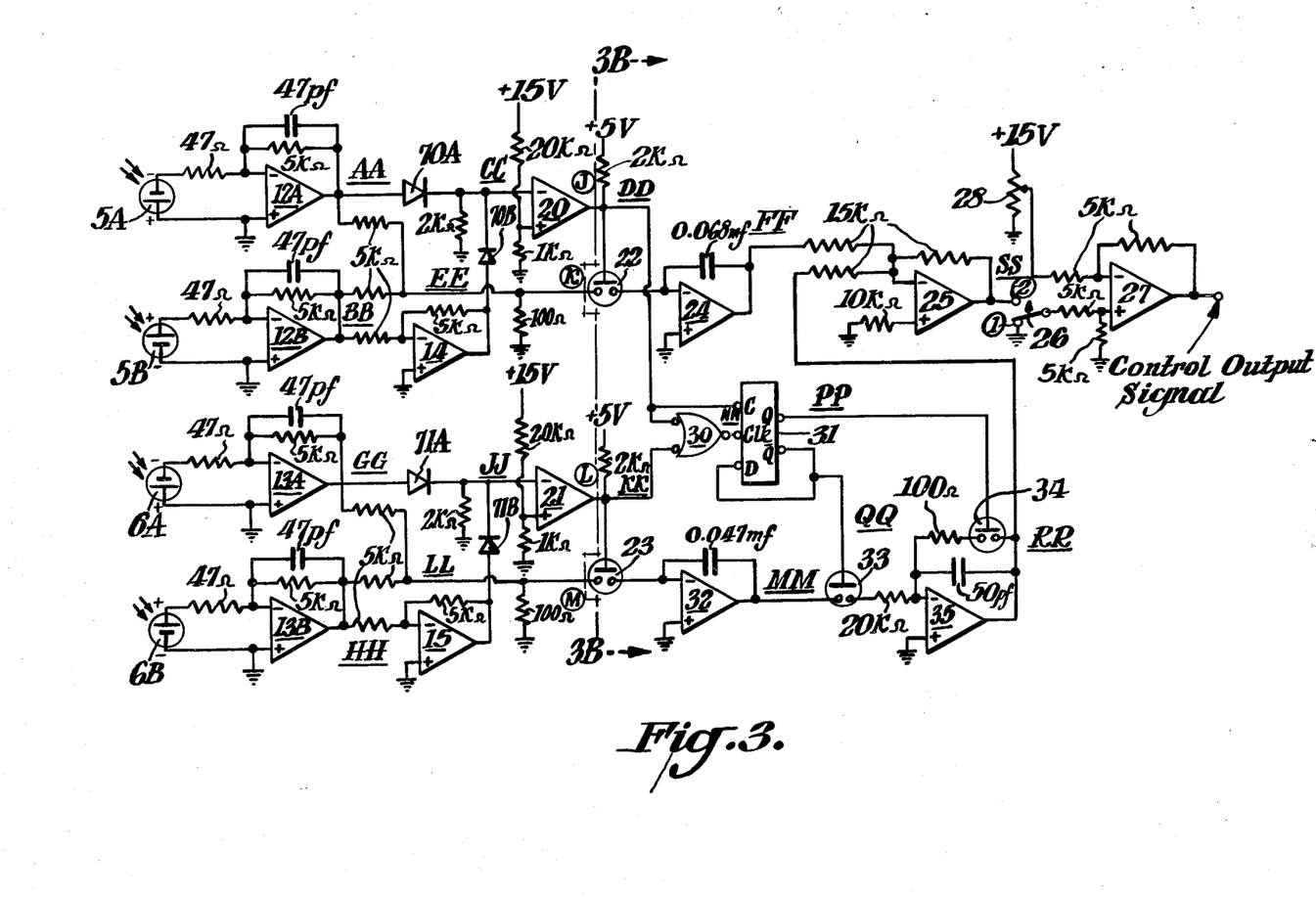
FIG. 3 is a schematic diagram of one embodiment of a control electronic circuit 10 having photocell-generated error signals input used with the apparatus of FIG. 1.
Figure 3A:
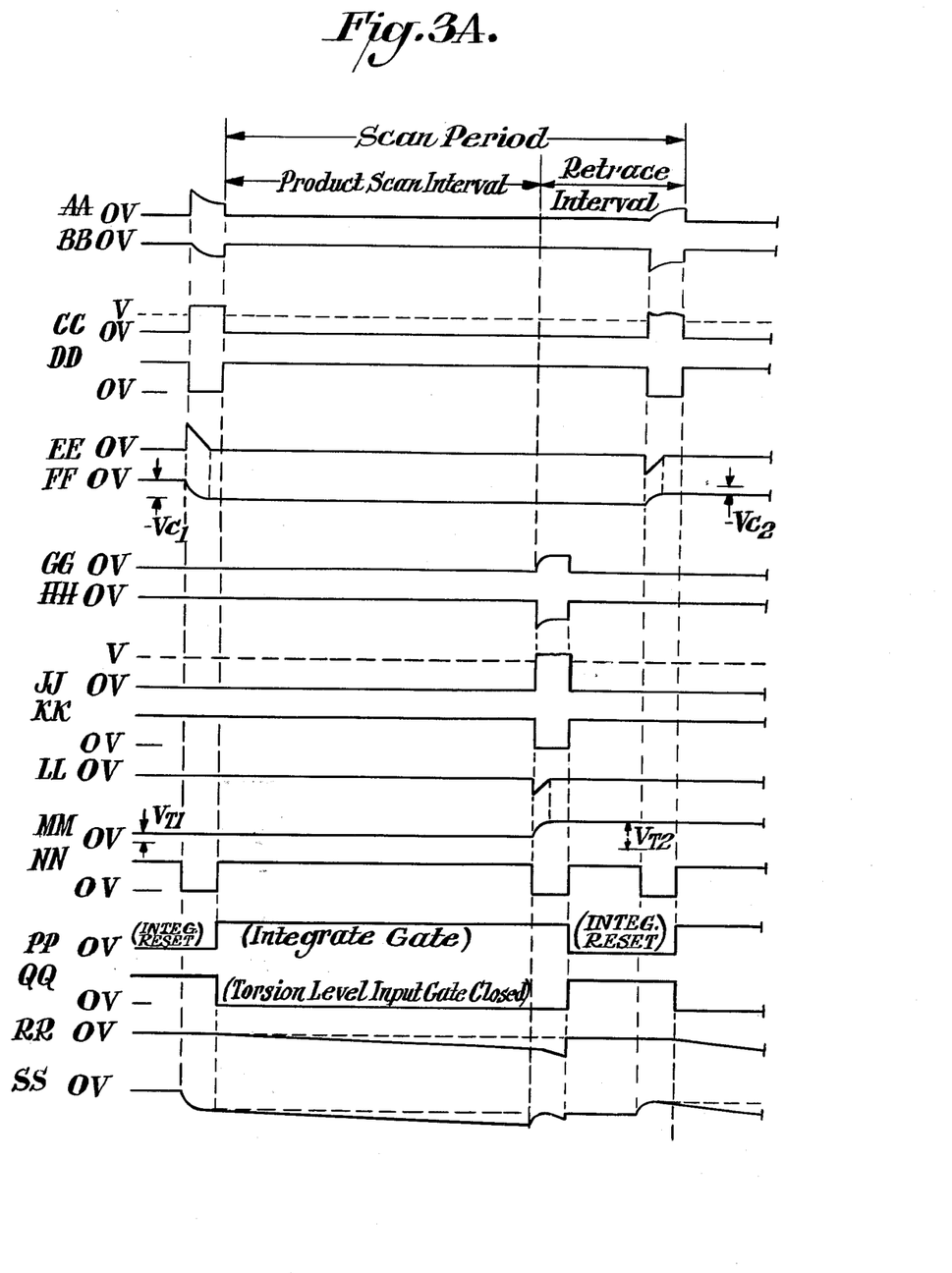
FIG. 3A is a drawing of typical electrical signal waveforms generated at various points in the system of FIG. 3.

Referring to FIG. 3, there is shown a preferred circuit for this invention, as to which FIG. 3A shows the waveforms which exist at the several points denoted, with zero voltage levels being, in all cases, indicated by the "OV" labels.

MD displacement photocells 5A and 5B produce output signals having the waveforms AA and BB, respectively, as the scanning spot 1b passes over them from left to right as seen in FIG. 1 at the beginning of any given web traverse. For purposes of this description it is assumed that, at the outset of the first scan, the spot 1b position overlies more of cell 5A than cell 5B, whereas at the outset of the next scan, the reverse is true. These variations are typical of scan-to-scan mirror facet cone angle differences.

In like manner, as the scanning beam passes over torsion monitor cells 6A and 6B, the resulting signals, waveforms GG and HH, respectively, show the beam's initial position to lie more over photocell 6B than 6A.

The circuit of FIG. 3 is generally conventional in nature, the resistance and capacitance values of the several components being shown adjacent each.

After amplification of the output signals from photocells 5A, 5B, 6A and 6B by the amplifiers 12A, 12B, 13A and 13B, respectively (the amplifiers typically being Teledyne-Philbrick Models TP 1421) to produce waveforms AA, BB, GG and HH and inversion of the outputs from amplifiers 12B and 13B by unity gain inverters (typically, Teledyne-Philbrick 1421 operational amplifiers) 14 and 15, respectively, the respective MD displacement and torsion monitor photocell signal paris are summed through two pairs of 1N 415 diodes, 70A, 70B and 71A, 71B, to give waveforms CC and JJ, respectively, thereby producing resultant signals having sufficient amplitudes on each scan to exceed the preset thresholds V of comparators 20 and 21, respectively (typically, National Semiconductor Models LM 211D). Comparators 20 and 21 in turn produce gating logic pulse signals, waveforms DD and KK, respectively, which are used to operate analog gates (typically, Siliconix DG 200 types) 22 and 23.

Simultaneously with the formation of the gating signals, the output signals from the MD displacement and torsion monitor amplifier pairs 12A, 12B and 13A, 13B, respectively, are differenced through the 5 Kohm resistors connected to the amplifier output terminals to produce error signals, waveforms EE and LL, which then pass to respective analog gates 22 and 23.

Waveforms EE and LL, FIG. 3A, show that both the MD displacement and the torsion error signals have been restored to zero baseline values before scan spot 1b leaves the surface of the corresponding photocell assembly. The ability of the control electronics 10 to restore the error signals to zero volt values is essential for complete scan-to-scan compensation from the effects of vibration and mirror facet variation. Therefore, selection of an appropriate beam deflector for a given scan rate and photocell assembly size should be based on its ability to return the scanning beam to its undeflected position before the beam completes its transit of the photocell surface.

Referring again to FIG. 3, in the calibration mode with SPDT switch 26 closed on its contact ①, potentiometer 28 is used to adjust the bias voltage furnished through amplifier 27 to driver 11 to obtain the required center frequency for the deflector 2 (determined by measurement of deflector efficiency v. frequency). Deflector 2 is mechanically adjusted to the Bragg angle that maximizes the intensity of the diffracted first order beam. Once this is obtained with switch 26 still in position ①, the scan beam is physically positioned to coincide with the junctions of component photocells 5A, 5B and 6A, 6B.

In the operating mode, switch 26 is closed on contact ② to permit the generated composite correction signals to be offset by the bias voltage value previously established in the calibrating mode to produce a composite scan tracking control output signal.

Thus, the MD displacement error signal pulses, waveform EE, after passing through analog gate 22, which is operated by concurrent control gate logic pulse signals at the beginning of each scan, waveform DD, are first integrated then held by integrator 24 to produce an integrated and held MD displacement error signal level $-V_{c_1}$ for the first scan and $-V_{c_2}$ for the second in waveform FF. These signal levels are then combined with the corresponding integrated torsion monitor error signals, waveform RR, in the 15 Kohm summing network interposed on the input side of inverter amplifier 25 (typically, a Teledyne-Philbrick 1421 operational amplifier) to generate a composite scan tracking control signal, waveform SS, from the two signal sources. Since the integrated torsion error signal, waveform RR, has a monotonically (i.e., the slope does not change sign throughout the range of interest) changing value in the course of each scan period, the resultant composite control signal SS will likewise contain a monotonically changing control component for maintaining each scan on its preselected transverse track across the inspected product web 14.

Where, as hereinbefore described, an MD displacement correction signal, waveform FF, was achieved by means of a single signal-gated integrator stage 24, the generation of the torsion correction signal waveform RR is obtained using two series-connected gated integrators 32 and 35 (typically, Teledyne-Philbrick 1421 operational amplifiers). These two integrating components are synchronized to operate in the following manner:

During the occurrence of gating logic signal, waveform KK, at the end of each scan, the torsion monitor analog gate 23 permits the torsion error signal, waveform LL, to pass to a first gated integrator 32 for integration. Then, when gate 23 opens, the value of the final integrated torsion error signal amplitude, shown in waveform MM, is held until its value is changed again at the end of the next scan. It should be noted that, in this example, waveform MM shows the integrated torsion error signal having an initial value of $V_{T1}$ prior to the integration interval and a final larger value of $V_{T2}$ after integration. This shows that an increased amount of correction is needed to maintain the scan on its path during the next scan.

The integrating and reset operations of the second torsion monitor gated integrator 35 are controlled by flip-flop 31. Logic pulse gating signals DD and KK, produced by comparators 20 and 21, respectively, at the beginning and end of each scan, respectively, are combined by inverting OR gate 30 to produce a clock signal, waveform NN, input to the CLK terminal of flip-flop 31 (typically, a Signetics 7474). A direct connection from the output of comparator 20 to terminal C of flip-flop 31 is used to ensure that a logic low level value is present at terminal Q for resetting integrator 35 to its zero volt baseline value by means of analog gate 34 at the outset of each scan, waveform PP. During the integrator reset interval, the complementary logic high signal appears on terminal $\overline{Q}$ of flip-flop 31, waveform QQ, this being used to open analog gate 33 at the input terminal of integrator 35 to disconnect it from the output terminal of gated integrator 32, which functions as a driving source. The shunt connection back to terminal D of flip-flop 31 is the flip-flop reset, operating when switch 33 opens. As the trailing edge of clock signal, waveform NN, coinciding with control gate logic signal waveform DD, causes flip-flop 31 to change state, gate 34 opens, gate 33 closes (gate 23 remaining open from the end of the preceding scan) and integrator 35 integrates the voltage imposed on its input terminal, which is that held by the 0.047 μfd capacitor of integrator 32 at the end of the last scan, thereby producing a monotonically increasing torsion correction signal, waveform RR. With terminal Q at an active logic low state, the trailing edge of the next pulse produced by torsion monitor gate signal, waveform KK, will reset flip-flop 31, open gate 33 and close analog gate 34 to initialize integrator 35. Since gate 23 closes before flip-flop 31 changes state, integrator 32 retains a new voltage level $V_{T2}$ of waveform MM which also changes the slope of waveform RR at the end of each scan with the cycle thereafter repeating for succeeding scans. The values of resistance and capacitance for integrator 35 are chosen to provide sub-critical correction (i.e., always some small amount of torsion monitor error present) for the scan speeds used in order to prevent over-correction and possible oscillation of the scan beam about its transverse path across the web.

Figure 2A:
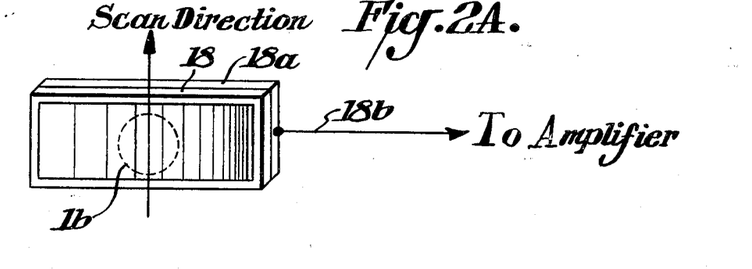
FIG. 2A is a partially schematic perspective view of a photocell amplitude-graded optical filter construction which can be utilized with the apparatus of FIG. 1.
Figure 3B:
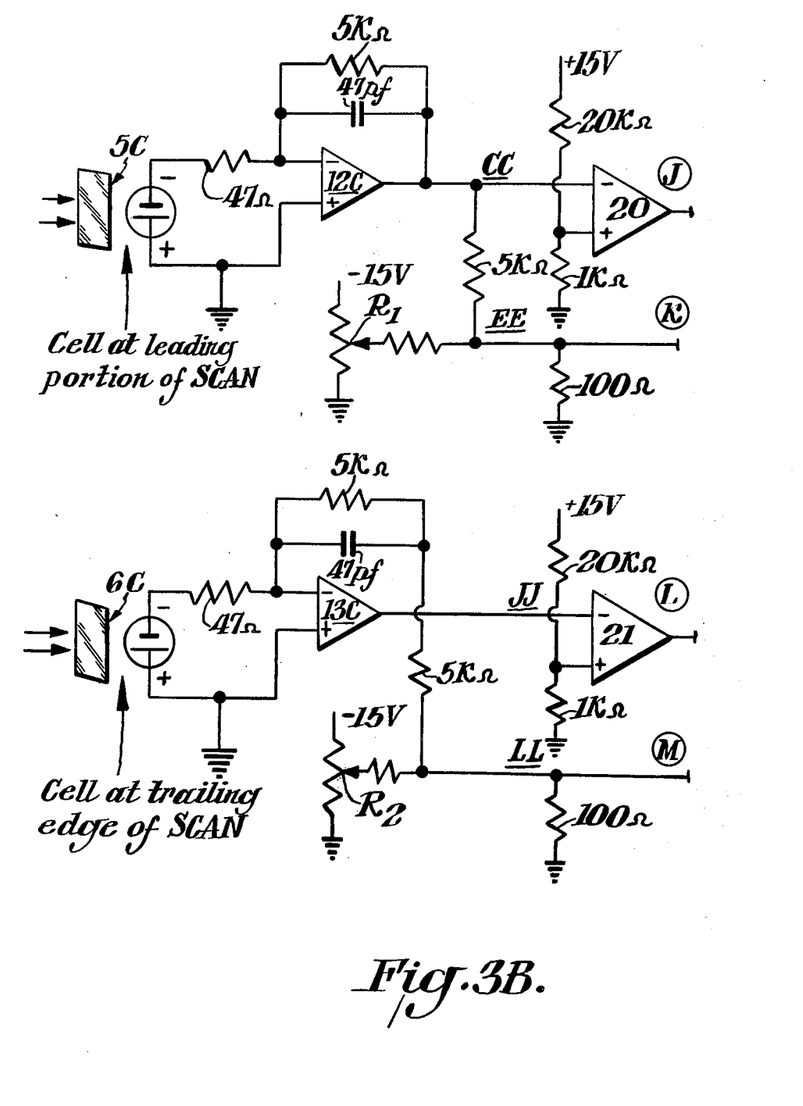
FIG. 3B is a schematic diagram of one embodiment of a control electronic circuit having photocell amplitude-graded optical filter-generated error signals input used with the apparatus of FIG. 1.

Referring to FIG. 3B, there is shown a preferred circuit for use where single amplitude-graded optical filter assemblies 5C and 6C, each overlying a photocell detector, are substituted for the dual photocells of FIG. 3. As shown in FIG. 2A, the amplitude gradient of each optical filter 18, typically Kodak Neutral Density Wedges of the group included in Kodak bulletin P-114 of 1971 rev. AX, are oriented normal to the scan direction so that the magnitude of the electrical signal passed to each amplifier (e.g., 12c, FIG. 3B) via lead 18b from photocell 18a is a function of the MD position of the scanning spot. The amplifiers required are reduced to two in number, 12C and 13C, which can be identical with 12A, 12B, 13A and 13B hereinbefore described, each provided with its own spot location potentiometers, $R_1$ and $R_2$, respectively. (Thus, $R_1$ sets the position of spot 1b prior to the commencement of the product scan, whereas $R_2$ sets the position after the scan.) The unity gain inverters 14 and 15, and the summing diodes of FIG. 3 can be dispensed with in this embodiment and the circuit to the right of line 3B—3B (FIG. 3), identical to that described for the FIG. 3 embodiment, is utilized for the subsequent signal processing. This embodiment has the disadvantage that its sensing accuracy is affected by laser source radiation intensity changes; however, where this does not occur, operation is entirely satisfactory.

Figure 4:
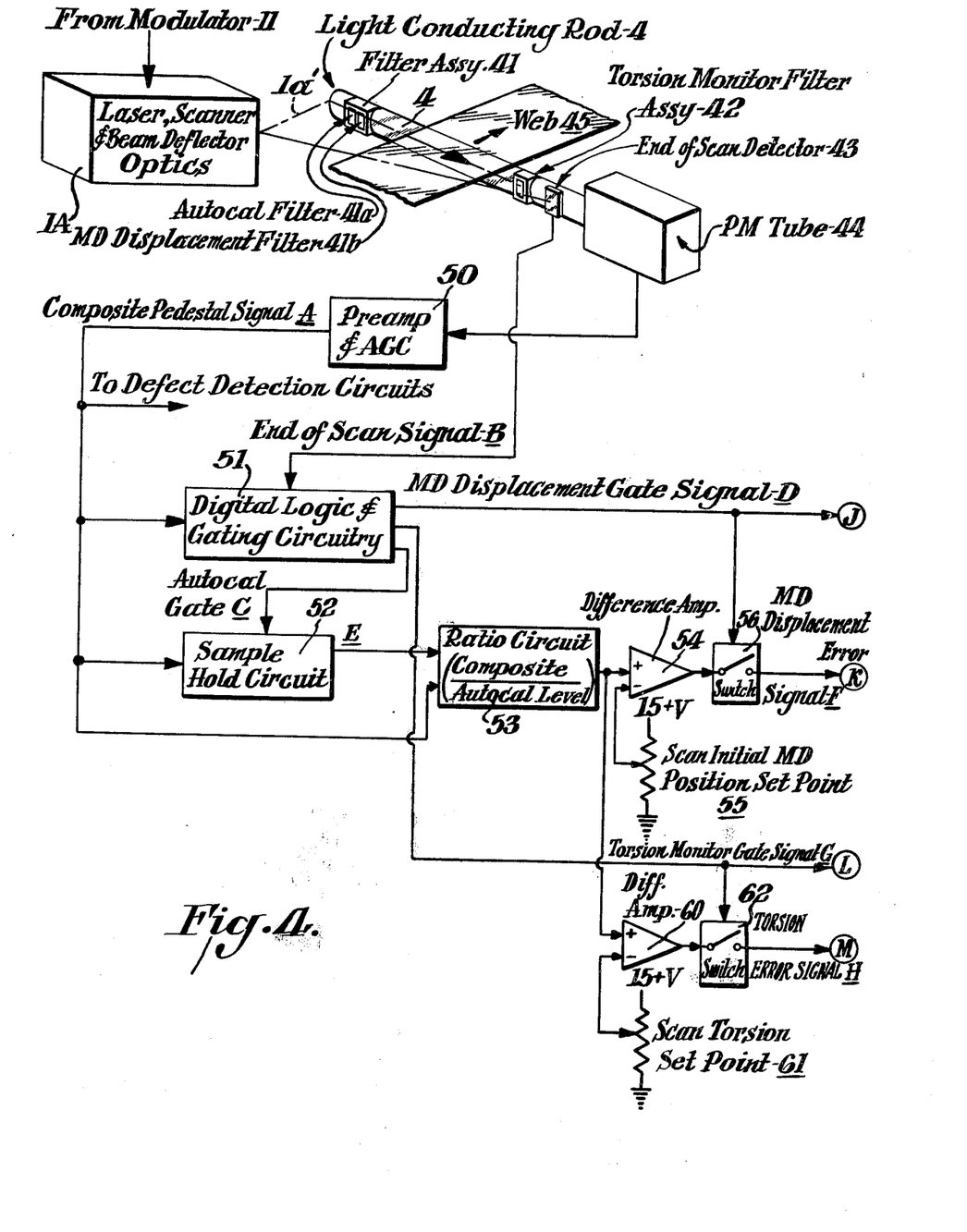
FIG. 4 is a partially schematic perspective view of a second embodiment of an inspector scan system utilizing amplitude-graded optical filters and an automatic calibrating (AUTOCAL) filter in conjunction with a light-collecting rod and accompanying ratio circuitry.
Figure 4A:
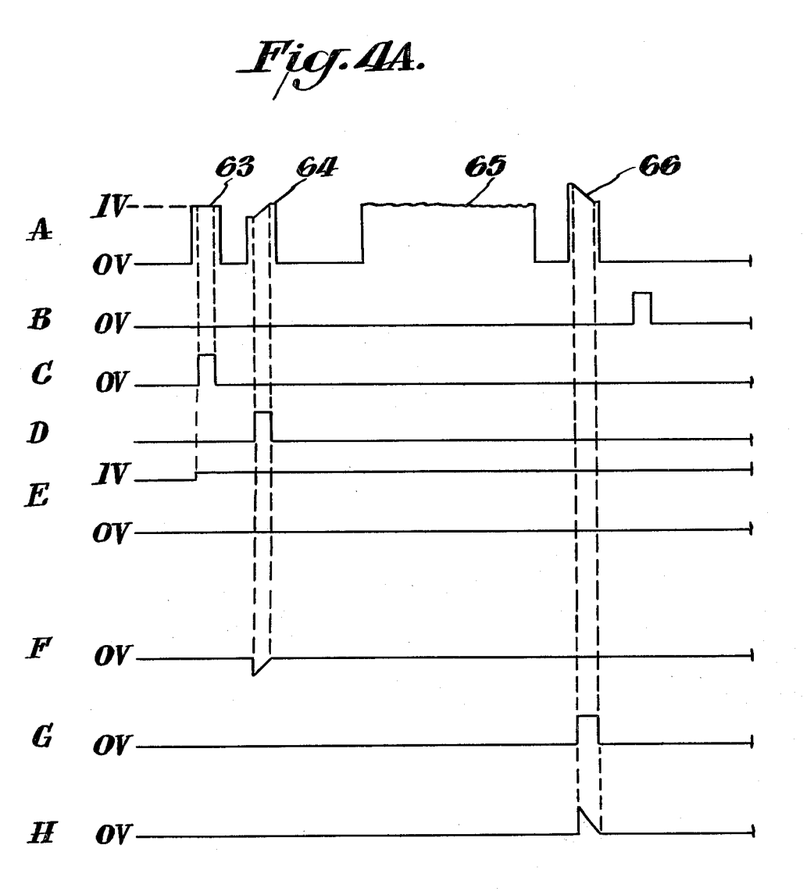
FIG. 4A is a drawing of typical electrical signal waveforms generated at various points in the system of FIG. 4.

FIG. 4 and the waveforms of FIG. 4A show another embodiment of this invention in which the relative magnitudes of the control and torsion monitor error signals are generated relative to the magnitude of an automatic calibration (AUTOCAL) signal which is established at the outset of each scan. A detailed description of the method and means used to generate the AUTOCAL signal is set out in U.S. Pat. No. 3,843,890 supra. In brief, the AUTOCAL signal is produced during the passage of scanning spot 1a' across an optical filter 41a disposed ahead of and off of the web. The changes in the level of transmitted radiation through filter 41a are detected and used to compensate the following product pedestal signal from the effects of optical gain variations before the product pedestal signal is discriminated.

In the described embodiment, the dual photocells of the design shown in FIG. 2, normally used to produce the MD displacement and torsion error signals, are replaced by two amplitude-graded optical filters, 41b and 42, of the design shown in FIG. 2A, but without associated photocells, in order to make full use of the sensing capability of the already gain-compensated photomultiplier tube 44. In the system shown in FIG. 4, Kodak Neutral Density Wedges of the type hereinbefore described as of Kodak bulletin P-114, 1971, rev. AX, design, again oriented normal to the scan direction, are used to generate the MD displacement error signal and the torsion error signal as hereinafter described.

In the FIG. 4 apparatus, a flying spot scanner and beam deflector 1A directs the first order diffracted monochromatic laser beam 1a' in a linear scan across the product web 45 along a path essentially parallel with the axis of stationary light-conducting rod 4 having filter assemblies 41 and 42 attached thereto. Filter assembly 41 comprises an AUTOCAL filter 41a and an MD displacement filter 41b, whereas filter assembly 42 comprises the torsion monitor filter. The two filter assemblies are respectively located adjacent the leading and trailing edges of running product web 45. The radiation transmitted through the filters and the web is collected by light-conducting rod 4 and conveyed to photomultiplier (PM) tube 44. The output signal from PM tube 44 is amplified and regulated by the preamplifier and AGC circuit 50 to produce a composite pedestal signal, waveform A, FIG. 4A (shown inverted).

As the scan beam 1a' passes rightwards, as seen in FIG. 4, a photocell end-of-scan detector 43 produces a timing signal, waveform B, which is used with certain edge events of composite pedestal signal waveform A to synchronize the timing of digital logic and gating circuit 51 with the corresponding position of the scan beam in the transverse (TD) direction. As described in full detail in U.S. Pat. No. 3,843,890 referred to supra, the primary function of the digital logic and gating circuit 51 is to generate the gating signals required to sample various portions of the composite signal, waveform A, for analysis. Three such gating signals are used with this invention, namely: AUTOCAL gating signal, waveform C; MD displacement gating signal, waveform D; and torsion monitor gating signal, waveform G.

Sample-hold circuit 52 uses AUTOCAL gating signal, waveform C to sample the magnitude of AUTOCAL pulse 63 of composite pedestal signal, waveform A, once each scan. The value is then held, as shown in waveform E, and used as the denominator term in ratio circuit 53 with the amplitude of composite pedestal signal, waveform A, forming the numerator. The output of ratio circuit 53 is now a gain-compensated composite pedestal signal which ensures that amplitude variations of the several component signals 64, 65 and 66 will vary about a predetermined value (dependent upon the AUTOCAL pulse 63 level set E, shown as 1 volt in FIG. 4A) regardless of fluctuations in optical gain. Thus, the MD displacement error signal, waveform F, obtained by differencing the magnitude of MD gain-compensated displacement portion, pulse 64, waveform A, with a predetermined machine direction scan position value by means of potentiometer 55, difference amplifier 54 and sampling switch 56, is a true measure of the amount of control needed to initiate each product scan at a predetermined MD position. In a similar manner, the torsion error signal, waveform H, is generated using potentiometer 61 and sampling switch 62 to obtain the difference between the gain-compensated torsion monitor component 66 of waveform A with a predetermined scan torsion set point value.

Computation of a combined integrated scan correction signal is achieved using the analog and logic circuitry at the output end of the control circuit shown in FIG. 3 by tying in MD displacement gate signal waveform D, MD displacement error signal, waveform F, torsion monitor gate signal, waveform G, and torsion monitor error signal H to the respective attachment points Ⓙ, Ⓚ, Ⓛ and Ⓜ, FIG. 3.

All of the embodiments hereinbefore described refer to the transmission mode of product inspection; however, application of the invention to the inspection of product webs using the reflection mode is equally practicable. In the latter case, filter assemblies 41 and 42, FIG. 4, or photocell assemblies 5A, 5B and 6A, 6B, FIG. 1, remain adjacent the two edges of the running web, but mirrors are then used where necessary to direct the light transmitted through the filters into the reflection channel rod collector 4. Such an arrangement is shown in FIG. 1B, U.S. Pat. No. 3,843,890 referred to supra.

While photosensitive detectors and graded-amplitude optical filter cells are hereinbefore described as used in pairs, it will be understood that photocells and graded-optical filter cells can be used in combination one with another if such arrangements are advantageous in given systems.

What is claimed is:

1. A closed loop control system for repetitively laterally repositioning a beam of radiation, which cyclically, transversely scans along a linear scan path, to a preselected scan path comprising
a first radiation sensitive detector located on only a beginning portion of said preselected scan path with its sensitive surface oriented towards said radiation beam, said radiation beam impinging on said sensitive surface and developing a momentary lateral position-dependent electrical signal having a distinctive portion thereof representative of coincidence of said radiation beam with said preselected scan path, means for storing said momentary electrical signal for the duration of each scan along said linear scan path, and radiation beam deflection means responsive to said stored electrical signal for laterally repositioning said radiation beam at the beginning of each scan into close conformity with said preselected scan path.

2. A closed loop control system for repetitively laterally repositioning a cyclically scanning beam of radiation to said preselected scan path according to claim 1 wherein said first detector is a dual cell type in which said radiation beam impinges concurrently on said dual cells, thereby developing said momentary electrical signal proportionate in magnitude to the area difference in which said radiation beam overlies one cell in comparison with the other.

3. A closed loop control system for repetitively laterally repositioning a cyclically scanning beam of radiation to a preselected scan path according to claim 1 wherein
said photosensitive detector consists of a photocell provided with an amplitude-graded filter overlying its photosensitive surface and containing and being graded normal to said scan path, said photocell developing a distinctive electrical signal level when said radiation beam coincides with said preselected scan path, and
radiation beam deflection means responsive to said momentary electrical signal bringing said radiation beam into close conformity with said preselected scan path defined by said distinctive electrical signal level.

4. A closed loop control system for repetitively laterally repositioning a cyclically scanning beam of radiation to a preselected scan path comprising
a first radiation sensitive detector located on only a portion of said scan path with its sensitive surface oriented towards said radiation beam, said radiation beam impinging on said sensitive surface and developing a momentary lateral position-dependent electrical signal having a distinctive portion thereof representative of coincidence of said radiation beam with said scan path, and radiation beam deflection means responsive to said electrical signal for laterally repositioning said radiation beam on each scan into close conformity with said scan path; said first detector is a dual cell type in which said radiation beam impinges concurrently on said dual cells, thereby developing said momentary electrical signal proportionate in magnitude to the area difference in which said radiation beam overlies one cell in comparison with the other; and
a second said radiation sensitive detector located at the end of said scan path for developing a momentary position-dependent electrical signal and wherein said radiation beam is monochromatic radiation and said deflection means comprises a voltage-controlled oscillator, said first detector being located at the beginning of said scan path, means responsive to said momentary position-dependent electrical signals only at the beginning and end of each scan, for generating a time varying beam displacement control voltage for input to said voltage-controlled oscillator, and an acousto-optical beam deflector responsive to said voltage-controlled oscillator bringing said radiation beam laterally and torsionally into close conformity with said preselected scan path.

5. In a flying spot web inspection system wherein a radiation spot is cyclically scanned along a linear scan path generally transverse to a running product web, a closed loop control system for repetitively laterally repositioning said radiation spot and hence said linear scan path to a preselected scan path comprising a photosensitive detector located off an edge of said web on only a beginning portion of said preselected scan path and having its photosensitive surface oriented toward said radiation beam, said radiation beam impinging on said photosensitive surface and developing a momentary lateral position-dependent electrical signal having a distinctive portion thereof representative of coincidence of said linear scan path with said preselected scan path, means for storing said momentary electrical signal for the duration of each scan along said linear scan path, and radiation beam deflection means responsive to said stored electrical signal for laterally repositioning said linear scan path into close conformity with said preselected scan path prior to each traverse of said product web.

6. In a flying spot web inspection system wherein a radiation spot is cylically scanned along a preselected scan path generally transverse to a running product web, a closed loop control system for repetitively laterally repositioning said radiation spot relative to said scan path comprising a photosensitive detector located off an edge of said web on only a beginning portion of said preselected scan path and having its photosensitive surface oriented toward said radiation beam, said radiation beam impinging on said photosensitive surface and developing a momentary lateral position-dependent electrical signal having a distinctive portion thereof representative of coincidence of said radiation beam with said preselected scan path, and radiation beam deflection means responsive to said momentary electrical signal for laterally repositioning said radiation beam into close conformity with said preselected scan path prior to each traverse of said product web; said closed loop control system is a machine direction compensation type provided, additionally, with a closed loop torsion monitor tracking means wherein said flying spot is repetitively laterally repositioned relative to said preselected path comprising a second photosensitive detector disposed along only a portion of and at the terminus of said preselected scan path off an edge of said web with its photosensitive surface oriented toward said radiation beam, said radiation beam impinging on said photosensitive surface and developing a position-dependent electrical signal, and radiation beam deflection means responsive to the composite of said closed loop machine direction control system signal and said closed loop torsion monitor tracking signal generated by said torsion monitor tracking means bringing said radiation beam into close conformity with said preselected path during the next following traverse of said product web.

7. In a flying spot web inspection system according to claim 5, a photosensitive detector consisting of a dual photocell.

8. A flying spot web inspection system according to claim 7 wherein said radiation spot is obtained from an essentially monochromatic source and said radiation beam deflection means comprises a voltage-controlled oscillator, means responsive to said momentary position-dependent electrical signals only at the beginning and end of each scan, for generating a time varying beam displacement control voltage for input to said voltage-controlled oscillator, and an acousto-optical beam deflector bringing said radiation beam and hence said linear scan path laterally and torsionally into close conformity with said preselected scan path.

9. In a flying spot web inspection system wherein a radiation spot is cyclically linearly scanned along a preselected scan path generally transverse to a running product web and the resulting product-modulated radiation is collected via a light-collecting rod delivering said radiation to photomultiplier means, and thence to product evaluation means including automatic calibrating means for said product-modulated radiation, and means for repetitively laterally repositioning said cyclically moving linearly scanning radiation spot to said preselected scan path comprising an amplitude-graded optical filter disposed along said preselected scan path off the leading edge of a web being inspected overlying said light conducting rod transmitting radiation therethrough generating, by impingement on said photomultiplier means, a momentary position-dependent electrical signal, means for storing said momentary electrical signal for the duration of each scan along said linear scan path, and radiation spot deflection means responsive to said stored position-dependent electrical signal bringing said linearly scanning radiation spot into close conformity with said preselected scan path.

10. A flying spot web inspection system according to claim 9 incorporating means developing electrical error signals restoring said linearly scanning radiation spot into close conformity with said preselected scan path at the outset of each scan, said error signals constituting ratios of an electrical analog output of said automatic calibration means and said momentary position-dependent electrical signals.

11. In a flying spot web inspection system wherein a radiation spot is cyclically scanned along a preselected scan path generally transverse to a running product web and the resulting product-modulated radiation is collected via a light-collecting rod delivering said radiation to photomultiplier means, and thence to product evaluation means including automatic calibrating means for said product-modulated radiation, and means for repetitively laterally repositioning said cyclically moving radiation spot to said scan path, comprising an amplitude-graded optical filter disposed along said scan path off the leading edge of a web being inspected overlying said light conducting rod transmitting radiation therethrough generating, by impingement on said photomultiplier means, a momentary position-dependent electrical signal, radiation spot deflection means responsive to said momentary position-dependent electrical signal bringing said radiation spot into close conformity with said preselected scan path, and a closed loop torsion monitor tracking means having a second amplitude-graded optical filter disposed along said scan path past the trailing edge of said web transmitting radiation through said light-collecting rod to said photomultiplier means, the composite signal obtained from said amplitude-graded optical filter at said leading edge of said web and said second amplitude-graded optical filter defining said preselected scan path over which said radiation beam is traversed repetitively across said product web.

12. A flying spot web inspection system according to claim 11 incorporating means developing electrical error signals restoring said radiation spot into close conformity with said preselected scan path constituting ratios of said composite signal with an electrical analog output of said automatic calibration means.

13. A flying spot web inspection system according to claim 12 wherein said radiation spot is obtained from an essentially monochromatic source and said radiation beam deflection means is of the acousto-optical type.

14. A flying spot web inspection system provided with a closed loop electrical machine direction scan compensating system and closed loop torsion monitor means developing, with said closed loop machine direction scan compensating system, a composite electrical error signal defining a predetermined linear path of flying spot travel transverse said web, and means constituting part of said closed loop torsion monitor means integrating the sensed torsion error signal to provide a monotonically increasing correction applicable to deflection means maintaining said flying spot on said predetermined path.

* * * * *